United States Patent [19]

Oliff et al.

[11] Patent Number: 5,047,502
[45] Date of Patent: Sep. 10, 1991

[54] GASTRIN RELEASING PEPTIDE ANTAGONIST

[75] Inventors: Allen I. Oliff, Gwynedd Valley, Pa.;
David C. Heimbrook, Ringoes, N.J.;
Mark W. Riemen, Doylestown, Pa.;
Victor M. Garsky, Blue Bell, Pa.

[73] Assignee: Merck and Co., Inc., Rahway, N.J.

[21] Appl. No.: 389,093

[22] Filed: Aug. 3, 1989

Related U.S. Application Data

[63] Continuation-in-part of Ser. No. 111,755, Oct. 23, 1987, abandoned.

[51] Int. Cl.$^5$ .......................... C07K 7/08; A61K 37/00
[52] U.S. Cl. ..................................... 530/329; 530/324
[58] Field of Search ..................... 514/2, 16; 530/329, 530/324

[56] References Cited

U.S. PATENT DOCUMENTS 4,350,627  9/1982  de Castiglione et al. .... 260/112.5 E

OTHER PUBLICATIONS

Marki et al., Peptides 2, Suppl. 2: 169-177 (1981).
Cuttitta et al., Nature, 316:823-826 (Aug. 29, 1985).

Primary Examiner—Lester L. Lee
Assistant Examiner—Avis Davenport
Attorney, Agent, or Firm—Frank P. Grassler; Donald J. Perrella; Hesna J. Pfeiffer

[57] ABSTRACT

Small cell lung carcinoma cells (SCLC) contain gastrin releasing peptide (GRP) receptors. The response of the cells to GRP is rapid growth. We have found a group of heptapeptides that act as GRP antagonists by blocking the binding of GRP to its receptor thereby inhibiting the growth of cells that are sensitive to the growth promoting acitivity of GRP.

15 Claims, No Drawings

GASTRIN RELEASING PEPTIDE ANTAGONIST

RELATED APPLICATION

This patent application is a continuation-in-part of copending patent application Ser. No. 111,755 filed Oct. 23, 1987, and now abandoned.

BACKGROUND OF THE INVENTION

Gastrin releasing peptide (GRP), a 27-amino acid hormone, stimulates the growth of small cell lung carcinoma (SCLC) cells in cell culture. Antibodies directed against GRP block the growth of SCLC in nude mice.

DISCLOSURE STATEMENT

Broccardo et al., Br. J. Pharmac. 55:221-227 (1975) compare the pharmacological activity of two natural bombesin-like peptides and 25 related synthetic peptides to that of bombesin.

Marki et al., Peptides 2, Suppl. 2:169-177 (1981) disclose structure activity relationship of 26 peptide analogs of bombesin and GRP. The minimal essential residues required for full potency of bombesin-like effects is represented by an acetylated C-terminal 8-peptide fragment wherein position 7 can be substituted by alanine, histidine, glutamine or D-glutamine. Modification of the tryptophan [8] and histidine [12] residues by alanine abolished the biological potency of these peptides. A blocked N-terminus is necessary for maximum response.

Moody et al., Peptides 4 (5):683-686 (1983) disclose the presence of high concentrations of bombesin-like peptides and receptors in small cell lung cancer (SCLC) and suggest that bombesin may function as an important regulatory agent in human SCLC.

Jensen et al., Nature 309:61-63 (May 3, 1984) diclose that a substance P analog is also a bombesin receptor antagonist.

Weber et al., J. Clin. Invest. 75:306-309 (1985) disclose that the mitogenicity of gastrin releasing peptide (GRP) resides in its carboxy terminal fragment, designated GRP 14-27, which is partly homologous to bombesin. The authors speculate that GRP or a closely related small peptide may be acting as an autocrine growth factor for SCLC.

Cuttitta et al., Nature, 316:823-826 (Aug. 29, 1985) disclose that a monoclonal antibody to bombesin blocks the binding of the hormone to cellular receptors and inhibits the clonal growth of SCLC in vitro and the growth of SCLC xenografts in vivo demonstrating that bombesin-like peptides can function as autocrine growth factors for human SCLC.

Corps et al., Biochem. J. 231:781-784 (1985) disclose that an analog of substance P inhibits the stimulation of DNA synthesis induced in Swiss 3T3 cells by bombesin.

Bepler et al., Cancer Research 47:2371-2375 (May 1, 1987) disclose that the undecapeptide physalaemin inhibits the clonal and mass culture growth of SCLC cell lines at picomolar concentrations.

Heinz-Erian et al., Am. J. Physiol. 252:G439-G442 (1987) disclosed that [D-Phe12] analogs of bombesin are the only bombesin receptor antagonists identified to date that interact only with the bombesin receptor.

OBJECTS OF THE INVENTION

It is an object of the present invention to provide peptide derivatives that act as antagonists of GRP. Another object of the present invention is to provide fragments of GRP that act as antagonists of GRP. Yet another object is to provide compounds that block the binding of GRP to the GRP cell receptor. A further object is to provide compounds of interest in studying the role of GRP in SCLC. These and other objects of the present invention will be apparent from the following description.

SUMMARY OF THE INVENTION

A series of peptide derivatives have been found which are GRP antagonists and which suppress GRP-stimulated mitogenesis in Swiss 3T3 cells.

The peptide of the present invention are the following:

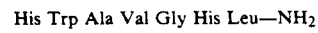

His Trp Ala Val Gly His Leu—NH$_2$

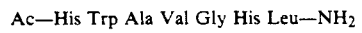

Ac—His Trp Ala Val Gly His Leu—NH$_2$

Ac—His Trp Ala Val Gly His Leu—NHR$^1$

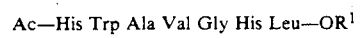

Ac—His Trp Ala Val Gly His Leu—OR$^1$ wherein R$^1$ is benzyl, a straight or branched chain alkyl group of from 1 to 5 carbon atoms, or a phenyl group either of which is optionally substituted by alkyl of from 1 to 3 carbons, hydroxy, alkoxy of from 1 to 3 carbons NH$_2$, halogen, trifluoromethyl or nitro.

DETAILED DESCRIPTION OF THE INVENTION

The activity of the peptides of the present invention as GRP antagonists was determined in competitive binding assays with a radioactive GRP derivative. Swiss 3T3 fibroblasts were used in these tests as the source of GRP receptor. Because these cells respond to GRP binding with a rapid increase in DNA synthesis, peptides that bind to the GRP receptor can also be tested for their ability to stimulate DNA synthesis. New DNA synthesis is one of the early steps in cell division and is widely accepted as a measure of mitogenicity or cell growth. Peptides which bind to the receptor and do not stimulate growth are then tested for their ability to block GRP stimulated DNA synthesis. Peptides which block DNA synthesis are mitogenic antagonists.

The binding of a peptide to its receptor initiates a series of changes within the cell which ultimately lead to more rapid cell growth. Many growth factors, including GRP, elicit an increase in intracellular calcium concentration ($[Ca^{2+}]i$) which may be part of the mitogenic signalling pathway (Heikkila et al., J. Biol. Chem. 262:16456-16460, 1987). Peptides which block the GRP dependent response in cells are GRP antagonists.

The peptides of the present invention can be synthesized from their constituent amino acids by conventional peptide synthesis techniques, preferably by solid-phase technology. The peptides are then purified by reverse-phase high performance liquid chromatography (HPLC).

Standard methods of peptide synthesis are disclosed, for example, in the following works: Schroeder et al., "The Peptides", Vol. I, Academic Press 1965, or Bodanszky et al., "Peptide Synthesis", Interscience Publishers, 1966, or McOmie (ed.) "Protective Groups in Organic Chemistry", Plenum Press, 1973, or Barany et al., "The Peptides: Analysis, Synthesis, Biology" 2, Chapter 1, Academic Press, 1980. The teachings of these works are hereby incorporated by reference.

Known peptide antagonists of GRP are based on the structure of bombesin, a GRP analog containing 14 amino acids, or substance P, which contains 11 amino acids. The size of these antagonists are such that pharmacokinetic problems may be encountered. In addition, antagonists based on substance P show cross-reactivity with the substance P receptor.

Current chemotherapeutic agents for the treatment of SCLC are poorly effective. The treatment of SCLC by inhibiting the binding of GRP to its receptor offers advantages over conventional chemotherapy. First, use of a peptide antagonist avoids the gross toxic side effects of conventional chemotherapy. In addition, receptor antagonists do not need to enter the cell to be effective.

The peptides of th present invention are effective in inhibiting the growth of cells that are sensitive to the growth promoting activity of GRP.

The following procedures were employed in determining the activity of the peptide derivatives of the present invention.

PROCEDURE A

Binding Inhibition Studies

Swiss 3T3 cells, obtained from Dr. K. Brown (Institute of Animal Physiology, Cambridge, U.K.). The cells were grown to confluency in Costar 12-well plates containing DMEM (Gibco) supplemented with 10% fetal bovine serum, 2 mM glutamine and 1% penicillin-streptomycin. The cells were washed twice with binding buffer [1:1 DMEM:Waymouths MB752/1 medium, plus 1 mg/ml BSA (Fraction V, Calbiochem)]. The antagonist was dissolved in 10 mM HCl, and diluted to the appropriate concentration in binding buffer. The antagonist was then added to the cells, followed by radiolabelled GRP at a final concentration of 7 nM. After 30 minutes incubation at 37° C., the supernatant liquid was removed and the cell monolayer rinsed four times with washing buffer (150 mM NaCl, 20 mM $Na_2HPO_4$, 5 mM KCl, 1.8 mM $KH_2PO_4$, 1 mg/ml BSA). The cells were then lysed with 1 ml/well of lysis buffer (1% Triton X-100, 0.1% BSA), and the solution was aspirated into scintillation vials for counting. Each data point was collected in triplicate.

PROCEDURE B

Mitogenic Stimulation

Swiss 3T3 cells were grown in monolayer culture in 24-well plates (Costar) in serum-free DMEM for 48 hours, at which time the peptide being tested and 23 nM $^3$H-thymidine were added. After an additional 48 hours, the cell monolayer was washed twice with PBS, and the cells were then removed with 1 ml 10× trypsin containing 5 mM EDTA. The cells were harvested with a Skatron filter apparatus, and the filters counted in a scintillation counter.

PROCEDURE C

Mitogenesis Inhibition

Swiss 3T3 cells were grown in monolayer culture in 24-well plates (Costar) in serum-free DMEM for 48 hours, at which time the GRP or a GRP homologue, the antagonist and 23 nM $^3$H-thymidine were added. After an additional 48 hours, the cell monolayer was washed twice with PBS, and the cells were then removed with 1 ml 10× trypsin containing 5 mM EDTA. The cells were harvested with a Skatron filter apparatus, and the filters counted in a scintillation counter.

PROCEDURE D

Stimulation of $Ca^{2+}$ Release in SCLC

Following the procedure of Heikkila et al., J. Biol. Chem. 262 16456 (1987), approximately $1 \times 10^8$ H345 SCLC cells, maintained in RPMI-1640 (Ro) medium supplemented with selenium, insulin, and transferrin, were harvested by settling and washing with Ro. They were then resuspended in 2 ml Ro, to which 1.2 nmol Fura-2/AM per $10^6$ cells was added. After a 15 minute incubation at 37° C., the cells were diluted to 10 ml with Ro and incubated for 1 hour at 37° C. The cells were then centrifuged and resuspended in HEPES-saline (140 mM NaCl, 5 mM KCl, 5 mM glucose, 1 mM $CaCl_2$, 1 mM $MgCl_2$, 20 mM HEPES, pH 7.4) at a density of $2.5-5 \times 10^6$ cells/ml. The cells were kept on ice for up to 2 hours before being used. $Ca^{2+}$ measurements were performed at 37° C. in an Aminco SPF-500 fluorimeter. The excitation wavelength was 340 nm, the emission wavelength 510 nm. Two ml of cell suspension was periodically resuspended in a 3 ml plastic cuvette. They were equilibrated at 37° C. for at least 5 minutes before data was collected. After a stable baseline was established, a mixture of the compound of interest an 100 nM GRP was added, and data was collected for approximately 5 minutes. At that time, a challenge dose of GRP was added, and data was collected for an additional 5 minutes. The cells were then lysed with 4 μl 10% Triton X-100 to measure peak flouorescence. Baseline fluorescence was measured after the subsequent addition of 40 μl 2M Tris (pH 9.5) and 64 μl 0.2M EGTA.

The following examples illustrate the present invention without, however, limiting the same thereto.

EXAMPLE 1

The following results were obtained following procedure C.

| Peptide Antagonist | Binding Inhibition | EC$_{50}$* Mitogenic Stimulation | Mitogenic Inhibition |
| --- | --- | --- | --- |
| Ac—His—Trp—Ala—Val—Gly—His—LeuNH2 (Acetyl GRP 20-26 Amide) | 2 uM | >100 uM | 3 uM |
| His—Trp—Ala—Val—Gly—His—LeuNH2 (GRP 20-26 amide) | 20 uM | >100 uM | 50 uM |

*EC$_{50}$ Definitions:

Binding Inhibition: [Antagonist] which reduces the specific binding of 7 nM [$^3$H-Phe$^{15}$] GRP 15-27 to 50% of the level observed in the absence of antagonist. Assay performed in Swiss 3T3 cell monolayers.

Mitogenic Stimulation: [Agonist] which stimulates uptake of $^3$H-thymidine to 50% of the maximal level caused by [Nle$^{27}$] GRP 15-27. Assay performed on Swiss 3T3 monolayers.

Mitogenic Inhibition: [Antagonist] which reduces the uptake of $^3$H-thymidine caused by 7 nM [Nle$^{27}$] GRP 15-27 to 50% of the level observed in the absence of antagonist. Similar results obtained for the first antagonist using [Nle$^{27}$] GRP 1-27 as the mitogen. Assay performed on Swiss 3T3 monolayers.

EXAMPLE 2

A suspension of the peptide N-acetyl His Trp Ala Val Gly His Leu, which was synthesized by standard peptide synthesis protocols, at 1 mg/ml in dry ethanol at 0° C. was deaerated by bubbling with dry N$_2$. Dry HCl gas was then passed through the solution at 0° C. until fuming was observed. The reaction vessel was capped, and then stirred at 0° C. for 45 minutes. After the HCl was removed by bubbling with dry N$_2$, the solution was rotovapped to dryness three times. The product, N-acetyl His Trp Ala Val Gly His Leu-OCH$_2$CH$_3$, was purified by HPLC.

The following IC$_{50}$ values for this compound were obtained in the indiated biological assay:

Binding inhibition: 3.9 nM (average of 6 experiments).

Mitogenic Stimulation: none (at concentrations up to 30 μM).

Mitogenic Inhibition: 15 nM (average of 2 experiments) [Ca$^{2+}$]i in SCLC: 400 nM.

EXAMPLE 3

The methyl ester of N-acetyl His Trp Ala Val Gly His Leu was synthesized as described in example 2 except substituting methanol for ethanol. The other esters in the following table were prepared by coupling N-acetyl His Trp Ala Val Gly with the corresponding His Leu-OR using 1-(3-dimethylaminopropyl)-3-ethylcarbodiimide hydrochloride. The intermediates, His Leu-OR, were obtained by condensation of (S)-Leu-OR with N$^\alpha$-N$^{im}$-diBoc-(S)-His by the mixed anhydride procedure followed by deprotection with anhydrous HCl in ethyl acetate. The initial leucine esters were prepared by esterification of Boc-(S)-Leu with the appropriate alcohol, 1-cyclohexyl-3-(2-morpholinoethyl)-carbodiimide metho-p-toluenesulfonate and N,N-dimethylaminopyridine in methylene chloride. The Boc protective group was subsequently removed with anhydrous HCl at 0° C. All peptides were purified by reverse-phase HPLC (>98% pure). Amino acid composition data were obtained in triplicate, and were consistent with the predicted sequence. N-Acetyl His Trp Ala Val Gly His Leu-NHEt was synthesized from the corresponding His-ethyl amide utilizing coupling procedures analagous to those described above.

The assays of example 2 were repeated with the following peptide derivatives with the results indicated:

|  | Binding Inhibition IC$_{50}$ | Mitogenic at IC$_{50}$ | Mitogenic Inhibition a IC$_{50}$ |
|---|---|---|---|
| AcHisTrpAlaValGlyHisLeu—OCH$_3$ | 7.7 | — | + |
| AcHisTrpAlaValGlyHisLeu—O(CH$_2$)$_2$CH$_3$ | 3.5 | — | + |
| AcHisTrpAlaValGlyHisLeu—O(CH$_2$)$_3$CH$_3$ | 6.8 | — | + |
| AcHisTrpAlaValGlyHisLeu—O(CH$_2$)$_4$CH$_3$ | 12.4 | — | + |
| AcHisTrpAlaValGlyHisLeu—OCH$_2$(CH$_3$)$_2$ | 38 | — | + |
| AcHisTrpAlaValGlyHisLeu—OCH$_2$C$_6$H$_5$ | 5.4 | — | + |
| AcHisTrpAlaValGlyHisLeu—NCH$_2$CH$_3$ | 53 | — | + |

What is claimed is:

1. A peptide having the amino acid sequence

His Trp Ala Val Gly Leu—NH$_2$,
Ac-His Trp Ala Val Gly Leu—NH$_2$,
Ac-His Trp Ala Val Gly Leu—NHR$^1$ or
Ac-His Trp Ala Val Gly Leu—OR$^1$ wherein R$^1$ is benzyl, a straight or branched chain alkyl group of from 1 to 5 carbon atoms, or a phenyl group, either of which is optionally substituted by alkyl of from 1 to 3 carbon atoms, hydroxy, alkoxy of from 1 to 3 carbon atoms, NH$_2$, halogen, trifluoromethyl or nitro.

2. A receptor-ligand complex formed by binding a peptide of claim 1 to a GRP receptor of a SCLC cell.

3. A method of inhibiting the growth of cells that are sensitive to the growth promoting activity of GRP which comprises treating the cells with a peptide of claim 1 in an amount effective to antagonize the growth promoting activity of GRP.

4. A peptide according to claim 1 having the amino acid sequence His Trp Ala Val Gly His Leu-NH$_2$.

5. A peptide according to claim 1 having the amino acid sequence Ac-His Trp Ala Val Gly His Leu-NH$_2$.

6. A peptide according to claim 1 having the amino acid sequence Ac-His Trp Ala Val Gly His Leu-NHR$^1$ wherein R$^1$ is benzyl, a straight or branched chain alkyl group of from 1 to 5 carbon atoms, or a phenyl group, either of which is optionally substituted by alkyl of from 1 to 3 carbon atoms, hydroxy, alkoxy of from 1 to 3 carbon atoms, NH$_2$, halogen, trifluoromethyl or nitro.

7. A peptide according to claim 1 having the amino acid sequence Ac-His Trp Ala Val Gly His Leu-OR$^1$ wherein R$^1$ is benzyl, a straight or branched chain alkyl group of from 1 to 5 carbon atoms, or a phenyl group, either of which is optionally substituted by alkyl of from 1 to 3 carbon atoms, hydroxy, alkoxy of from 1 to 3 carbon atoms, NH$_2$, halogen, trifluoromethyl or nitro.

8. A peptide according to claim 1 having the amino acid sequence:

AcHisTrpAlaValGlyHisLeu-OCH$_3$,

AcHisTrpAlaValGlyHisLeu-O(CH$_2$)$_2$CH$_3$,

AcHisTrpAlaValGlyHisLeu-O(CH$_2$)$_3$CH$_3$,

AcHisTrpAlaValGlyHisLeu-O(CH$_2$)$_4$CH$_3$,

AcHisTrpAlaValGlyHisLeu-OCH$_2$(CH$_3$)$_2$,

AcHisTrpAlaValGlyHisLeu-OCH$_2$C$_6$H$_5$ or

AcHisTrpAlaValGlyHisLeu-NCH$_2$CH$_3$.

9. A peptide according to claim 8 having the amino acid sequence:

AcHisTrpAlaValGlyHisLeu-OCH$_3$.

10. A peptide according to claim 8 having the amino acid sequence:

AcHisTrpAlaValGlyHisLeu-O(CH$_2$)$_2$CH$_3$.

11. A peptide according to claim 8 having the amino acid sequence:

AcHisTrpAlaValGlyHisLeu-O(CH$_2$)$_3$CH$_3$.

12. A peptide according to claim 8 having the amino acid sequence:

AcHisTrpAlaValGlyHisLeu-O(CH$_2$)$_4$CH$_3$.

13. A peptide according to claim 8 having the amino acid sequence:

AcHisTrpAlaValGlyHisLeu-OCH$_2$(CH$_3$)$_2$.

14. A peptide according to claim 8 having the amino acid sequence:

AcHisTrpAlaValGlyHisLeu-OCH$_2$C$_6$H$_5$.

15. A peptide according to claim 8 having the amino acid sequence:

AcHisTrpAlaValGlyHisLeu-NCH$_2$CH$_3$.

* * * * *

UNITED STATES PATENT AND TRADEMARK OFFICE
CERTIFICATE OF CORRECTION

PATENT NO.  : 5,047,502
DATED       : September 10, 1991
INVENTOR(S) : Allen I. Oliff, David C. Heimbrook, Mark W. Riemen, and Victor M. Garsky It is certified that error appears in the above-identified patent and that said Letters Patent is hereby corrected as shown below:

Col. 5 and 6, claim 1, the four peptide sequences reading as follows:

```
"    His Trp Ala Val Gly Leu-NH2,
  Ac-His Trp Ala Val Gly Leu-NH2,
  Ac-His Trp Ala Val Gly Leu-NHR1 or
  Ac-His Trp Ala Val Gly Leu-OR1"
``` should read as follows:

```
"    His Trp Ala Val Gly His Leu-NH2,
  Ac-His Trp Ala Val Gly His Leu-NH2,
  Ac-His Trp Ala Val Gly His Leu-NHR1 or
  Ac-His Trp Ala Val Gly His Leu-OR1".
```

Signed and Sealed this

First Day of June, 1993

Attest:

MICHAEL K. KIRK

Attesting Officer

Acting Commissioner of Patents and Trademarks